United States Patent
Moskovits et al.

(10) Patent No.: US 8,427,639 B2
(45) Date of Patent: Apr. 23, 2013

(54) SURFACED ENHANCED RAMAN SPECTROSCOPY SUBSTRATES

(75) Inventors: Martin Moskovits, Santa Barbara, CA (US); Thomas Wray Tombler, Somerset, NJ (US); Robert Frank Koefer, Whitehall, PA (US)

(73) Assignee: Nant Holdings IP, LLC, Los Angeles, CA (US)

( * ) Notice: Subject to any disclaimer, the term of this patent is extended or adjusted under 35 U.S.C. 154(b) by 752 days.

(21) Appl. No.: 12/437,091

(22) Filed: May 7, 2009

(65) Prior Publication Data

US 2010/0284001 A1    Nov. 11, 2010

(51) Int. Cl.
G01J 3/44    (2006.01)

(52) U.S. Cl.
USPC .................................................. 356/301

(58) Field of Classification Search ............ 356/36, 356/301, 305
See application file for complete search history.

(56) References Cited

U.S. PATENT DOCUMENTS

| | | | |
|---|---|---|---|
| 7,151,598 B2 | 12/2006 | Poponin | |
| 7,158,219 B2 | 1/2007 | Li et al. | |
| 7,236,242 B2 | 6/2007 | Kamins et al. | |
| 7,245,370 B2 * | 7/2007 | Bratkovski et al. | 356/301 |
| 7,351,588 B2 | 4/2008 | Poponin | |
| 7,391,511 B1 | 6/2008 | Bratkovski et al. | |
| 7,466,406 B2 | 12/2008 | Mirkin et al. | |
| 7,638,431 B2 * | 12/2009 | Yasseri et al. | 438/678 |
| 7,738,096 B2 * | 6/2010 | Zhao et al. | 356/301 |
| 2004/0023046 A1 * | 2/2004 | Schlottig et al. | 428/469 |
| 2006/0038990 A1 * | 2/2006 | Habib et al. | 356/301 |
| 2006/0055922 A1 * | 3/2006 | Li et al. | 356/301 |
| 2006/0060472 A1 * | 3/2006 | Tomita et al. | 205/112 |
| 2006/0119853 A1 | 6/2006 | Baumberg et al. | |
| 2006/0146323 A1 * | 7/2006 | Bratkovski et al. | 356/301 |
| 2008/0174775 A1 * | 7/2008 | Moskovits et al. | 356/301 |

OTHER PUBLICATIONS

Zhao et al., "Polarized Surface Enhanced Raman and Absorbance Spectra of Aligned Silver Nanorod Arrays", J. Phys. Chem. B, 2006, 110, pp. 3153-3157.
Jeong et al., "Polarized Surface Enhanced Raman Scattering From Aligned Silver Nanowire Rafts", J. Phys. Chem B, 2004, 108 (34), pp. 12724-12728.
Tao et al., "Polarized Surface-Enhanced Raman Spectroscopy on Coupled Metallic Nanowires", J. Phys. Chem B, vol. 109, No. 33, 2005, pp. 15687-15690.
Prokes et al., "Formation of Ordered and Disordered Dielectric/Metal Nanowire Arrays and Their Plasmonic Behavior", US Naval Research Laboratory, pp. 1-13, PROC SPIE, vol. 6768E1 (2007).

* cited by examiner

*Primary Examiner* — Roy M Punnoose
(74) *Attorney, Agent, or Firm* — Fish & Associates, PC

(57) ABSTRACT

Manufacturing a surface enhanced Raman spectroscopy (SERS) active structure includes exposing a substrate to produce an exposure pattern then etching the substrate based on the exposure pattern to produce a plurality of nanostructure cores having a plurality of sides extending from the substrate. Adjacent nanostructure cores are separated by core gaps. SERS active material is deposited onto the plurality of nanostructure cores producing a structure having gaps suitable for use in a SERS process.

29 Claims, 17 Drawing Sheets

SURFACED ENHANCED RAMAN SPECTROSCOPY SUBSTRATES

FIELD OF THE INVENTION

The subject invention concerns nano-structured surfaces and in particular nano-structured surfaces that may be used for Surface Enhanced Raman Spectroscopy (SERS).

BACKGROUND OF THE INVENTION

Raman spectroscopy is a light scattering effect from a monochromatic light source, usually a laser wherein the light impinges upon molecules of a material being analyzed (analyte) and excites electrons of the analyte into a virtual state. Raman light is observed when the electron returns to its base state. Normally, the Raman effect is too weak to be used as a tool to sense and identify a small number of molecules. However, in the presence of a nanostructured material that exhibits SERS activity, the Raman effect may be greatly enhanced. A SERS active structure typically consists of a SERS active material, such as gold or silver having nanostructure features.

SUMMARY OF THE INVENTION

The present invention is embodied in a surface enhanced Raman spectroscopy (SERS) system which includes a nano-structured substrate. The substrate includes multiple nanostructures extending from the substrate, each of the plurality of nanostructures including a core and a coating of SERS active material covering at least a portion of the core. The multiple cores on the substrate are separated from each other by core gaps and the SERS active material on adjacent cores is separated by SERS gaps. The SERS gaps are sufficiently small for the material to be effective in a SERS process.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The nanostructure features may be formed on a substrate so that there are small SERS gaps separating adjacent SERS active elements. The SERS active elements are spaced by the small gaps so that one or more molecules may be positioned between two adjacent nanostructures for performing SERS. It is difficult to make SERS active structures because of the size of the SERS gaps between the adjacent nanostructure elements. This spacing, which may be on the order of 1 nm to 50 nm, is difficult to make in a production environment.

Figure 1A:
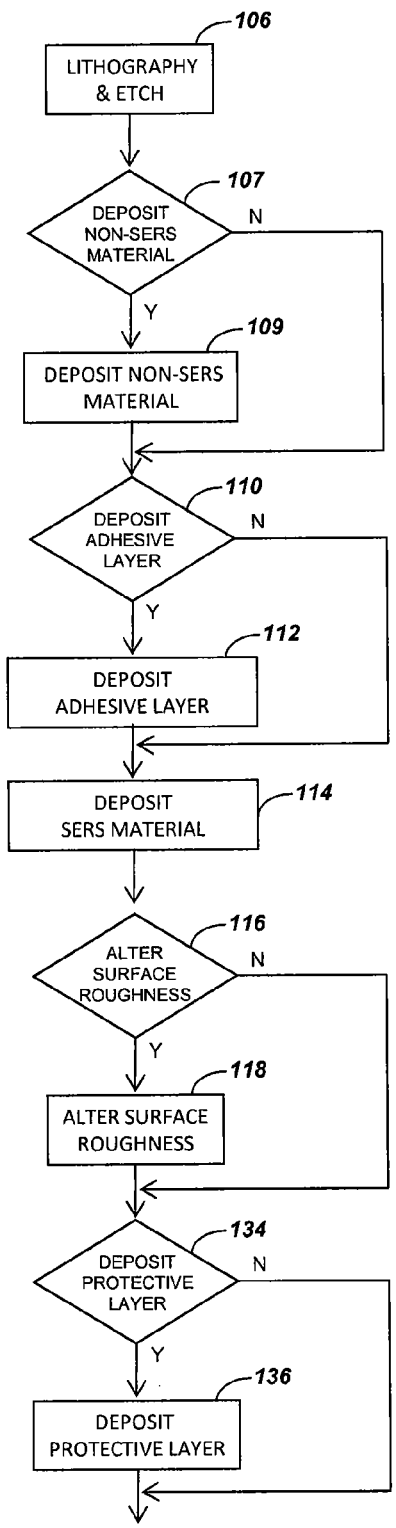
FIG. 1A is a flow-chart diagram of method for manufacturing a SERS active structure.

FIG. 1A is a flow-chart diagram of a procedure for manufacturing a SERS active structure in accordance with an embodiment of the invention. The first step in this procedure is to select the type of substrate from which or on which the SERS-active nanostructures are to be formed. It is contemplated that the substrate may be made entirely of a SERS-active material or it may be made of a material that does not exhibit SERS activity but which is then coated with a SERS-active material. In addition, the nanostructures may be formed in the substrate or on top of the substrate.

The substrate may be monolithic (e.g. a single-crystal silicon wafer) or it may be a multi-layer element having a nanostructure layer formed on top of a substrate. The substrate may be any one of (glass, fused silica, quartz, silicon oxide, silicon, gallium arsenide, aluminum oxide, germanium or sapphire). The nanostructure layer may be formed as an one of (silicon oxide, silicon, aluminum oxide, metal oxide, metal, or other dielectric or semiconductor material). In addition, it is contemplated that either the nanostructure layer or the entire device may be formed of a SERS active material such as Silver or Gold. Where the nanostructure layer is different from the substrate, there may be an etch-stop layer between the nanostructure layer and the substrate. For example, an etch-stop layer of $HfO_2$ may be deposited on a substrate and an $SiO_2$ microstructure layer may be formed on the etch-stop layer. The microstructure cores may then be formed in the $SiO_2$ layer, as described below, using an etchant that preferentially etches $SiO_2$ relative to $HfO_2$.

The substrate may be processed using photolithographic techniques to produce an array of nanostructures. The nanostructure array may be one-dimensional (1D) or two-dimensional (2D), as described below. The first step in the photolithographic process is, at step 106, the substrate or nanostructure layer, coated with a photoresist, is exposed to create a pattern that conforms to the desired nanostructure array. After the photoresist is exposed, the portion not corresponding to the nanostructure array is removed and the substrate is etched to form nanostructure cores.

Figure 1B:
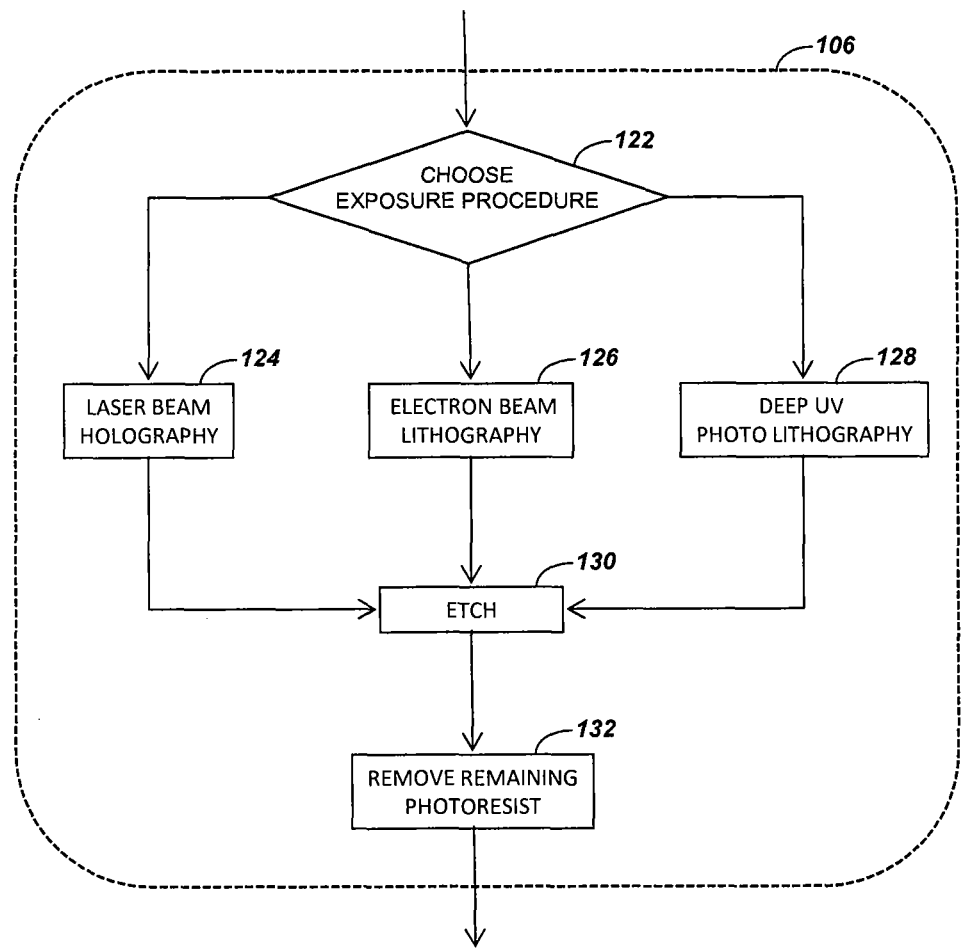
FIG. 1B is a flow-chart diagram of the patterning process in FIG. 1A.

Details on exposure and etching are shown in the block diagram of FIG. 1B. The particular photolithography technique is then chosen in step 122. Photolithography can be performed by laser beam holography in step 124, electron beam lithography in step 126 or deep ultra-violet (DUV) photolithography in step 128. During photolithography, the photo resist is exposed to a radiation source to form an exposure pattern. The exposure pattern defines the shapes of the nanostructures. As described above, the portion of the photoresist that does not conform to the nanostructure array is removed.

Once the photoresist is removed, etching techniques such as wet etching or dry etching, in step 130, may be utilized to remove portions of the nanostructure layer or of the substrate between the nanostructure elements. By removing this material from the nanostructure layer or from the substrate, one dimensional (1-D) or two dimensional (2-D) nanostructure cores may be constructed. These etching techniques are desirably anisotropic to ensure that the nanostructure cores are not undercut. After etching is complete, the remaining photoresist on the substrate or nanostructure layer 204 may then be removed, at step 132, before further manufacturing.

Figure 2:
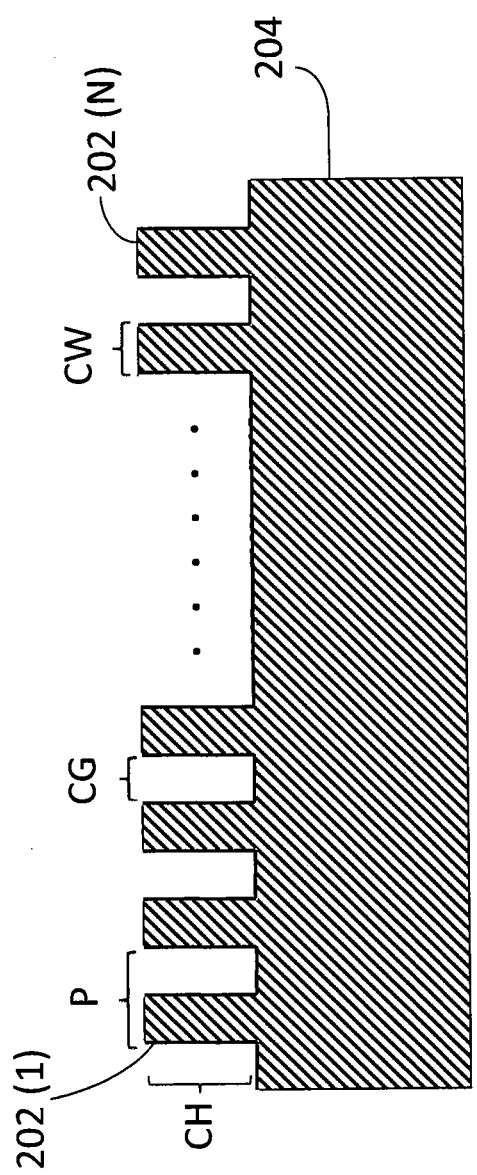
FIG. 2 is a cross sectional view of a substrate with nanostructure cores.

FIG. 2 is a cross sectional view of a substrate 204 with nanostructure cores 202(1)-202(N). This structure is illustrated as having monolithic cores, that is to say, cores formed from the substrate material. It is contemplated, however, that the structure may be formed in a deposited or grown nanostructure layer (not shown in FIG. 2) on top of the substrate.

The nanostructure cores have a core height CH and core width CW. The cores are also formed on substrate 204 at a uniform pitch P and separated by a core gap CG. In one embodiment, the cores are preferably constructed having a CG ranging from 50 nm-500 nm. It is noted, however, that P (50 nm to 10 microns) and CW may range between 10 nm and 10 microns; CH may range from 10 nm to 10 microns or more and CG may range from 1 nm-500 nm.

If the SERS structure is monolithic, then the nanostructure cores are etched directly from the substrate 204. If the SERS structure is not monolithic, then the nanostructure cores are etched from an material layer that is deposited or grown on the substrate 204. Thus, the nanostructure cores 202(1)-202(N) may be the same material as the substrate, or different material than the substrate.

Figure 3:
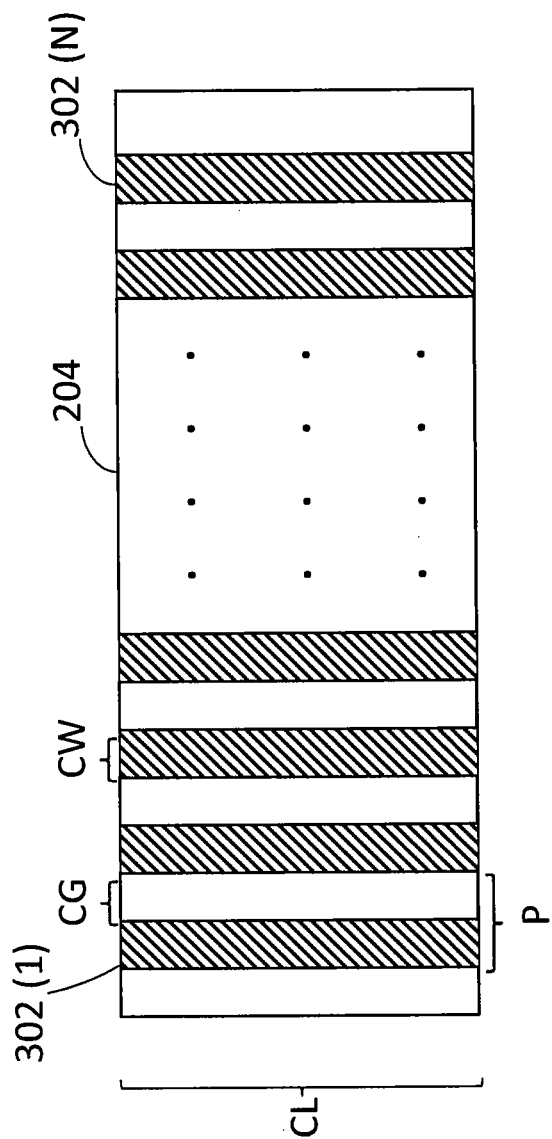
FIG. 3 is a top view of a substrate with nanowire cores.

FIG. 3 shows a top view of nanostructure cores that are constructed as nanowire cores 302(1)-302(N). The parallel nanowires cores are constructed to produce a uniform 1-D grating array to which each nanowire core extends a distance CL across the width of substrate 204.

The 1-D grating array in FIG. 3 may be constructed by any of the various lithography techniques described in FIG. 2. Specifically, during laser interference holography, or electron beam lithography, the 1-D exposure pattern for the nanowire cores may be traced by directing the radiation source at a right angle and a uniform pitch with respect to the substrate 204. During DUV lithography, an optical mask may be constructed to direct the ultra-violet light in the 1-D exposure pattern. Another alternative may be to use contact printing to selectively form the pattern in photoresist on the substrate.

The substrate may also be rotated at a second perpendicular angle with respect to substrate 204, thereby producing a 2-D exposure pattern. Specifically, a 2-D exposure pattern of square nanopillar cores as shown in FIG. 4a may be realized.

During DUV lithography, the optional mask may be constructed to produce a similar exposure pattern for realizing the 2-D nanopillar cores. The 2-D square cores 402(2,1)-402(N-1,N) in FIG. 4a are constructed with a set core width CW, core length CL, vertical pitch PV and horizontal pitch PH.

Figure 4A:
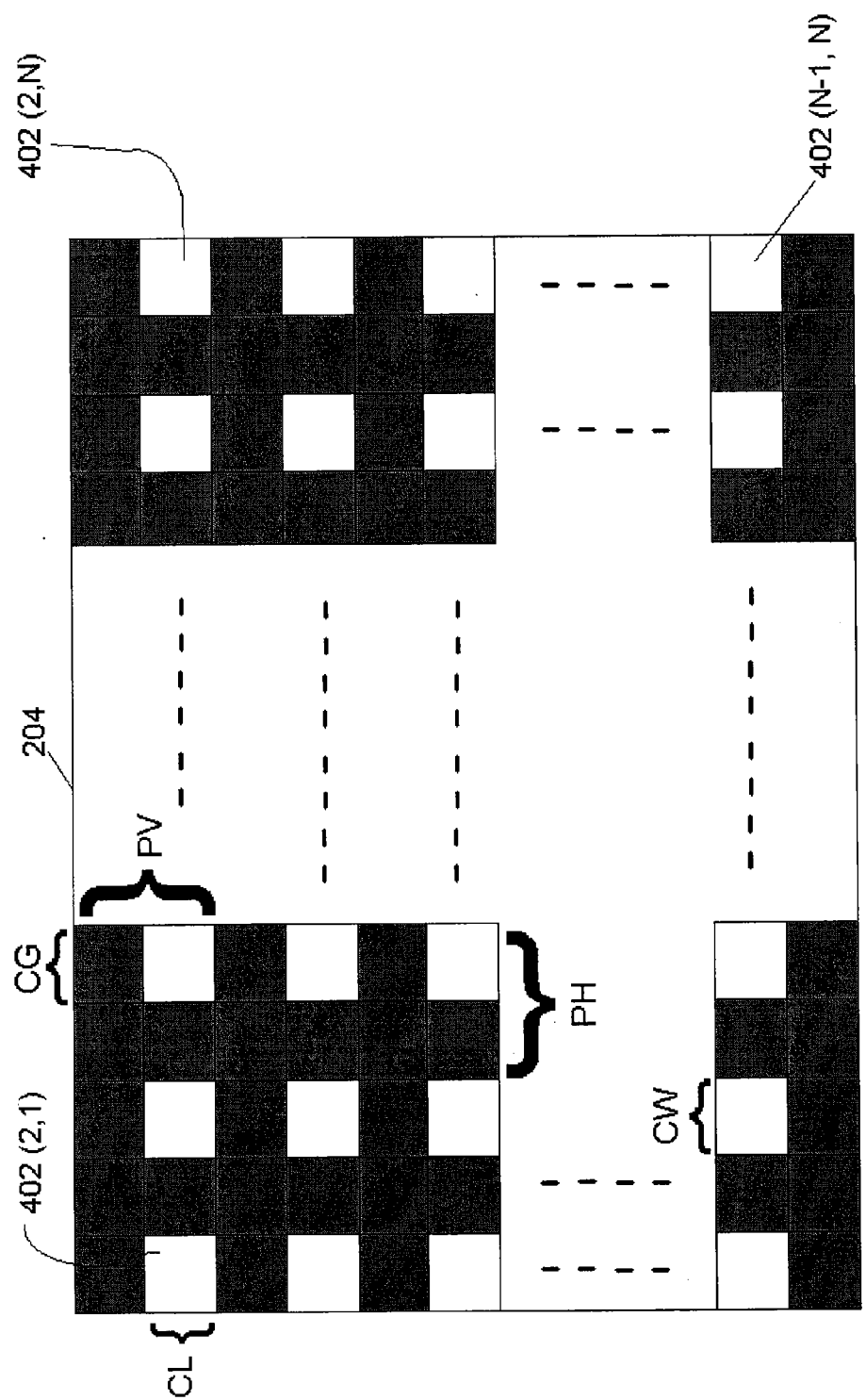
FIG. 4A is a top view of a substrate with square nanopillar cores.
Figure 4B:
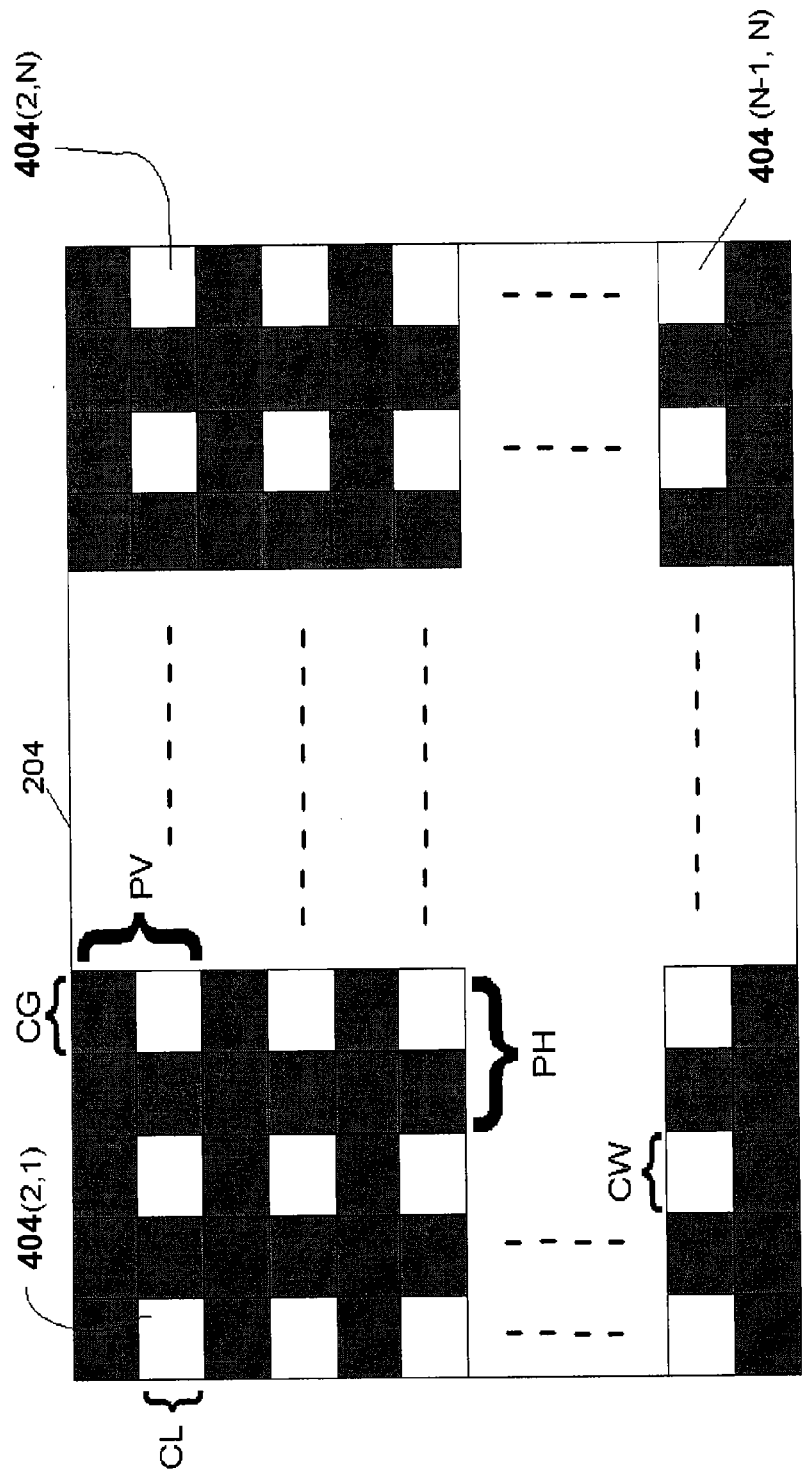
FIG. 4B is a top view of a substrate with rectangular nanopillar cores.

Although in FIG. 4a, the vertical and horizontal pitches are approximately the same, thereby producing substantially square cores, it should be noted that the vertical and horizontal pitches PV and PH may not be the same. By setting different pitches, the 2-D nanopillars may have rectangular shapes. FIG. 4b shows an example of rectangular nanostructure cores formed by setting the horizontal pitch PH to be greater than the vertical pitch PV. This results in rectangular nanopillar cores 404(2,1)-404(N-1,N).

Figure 4C:
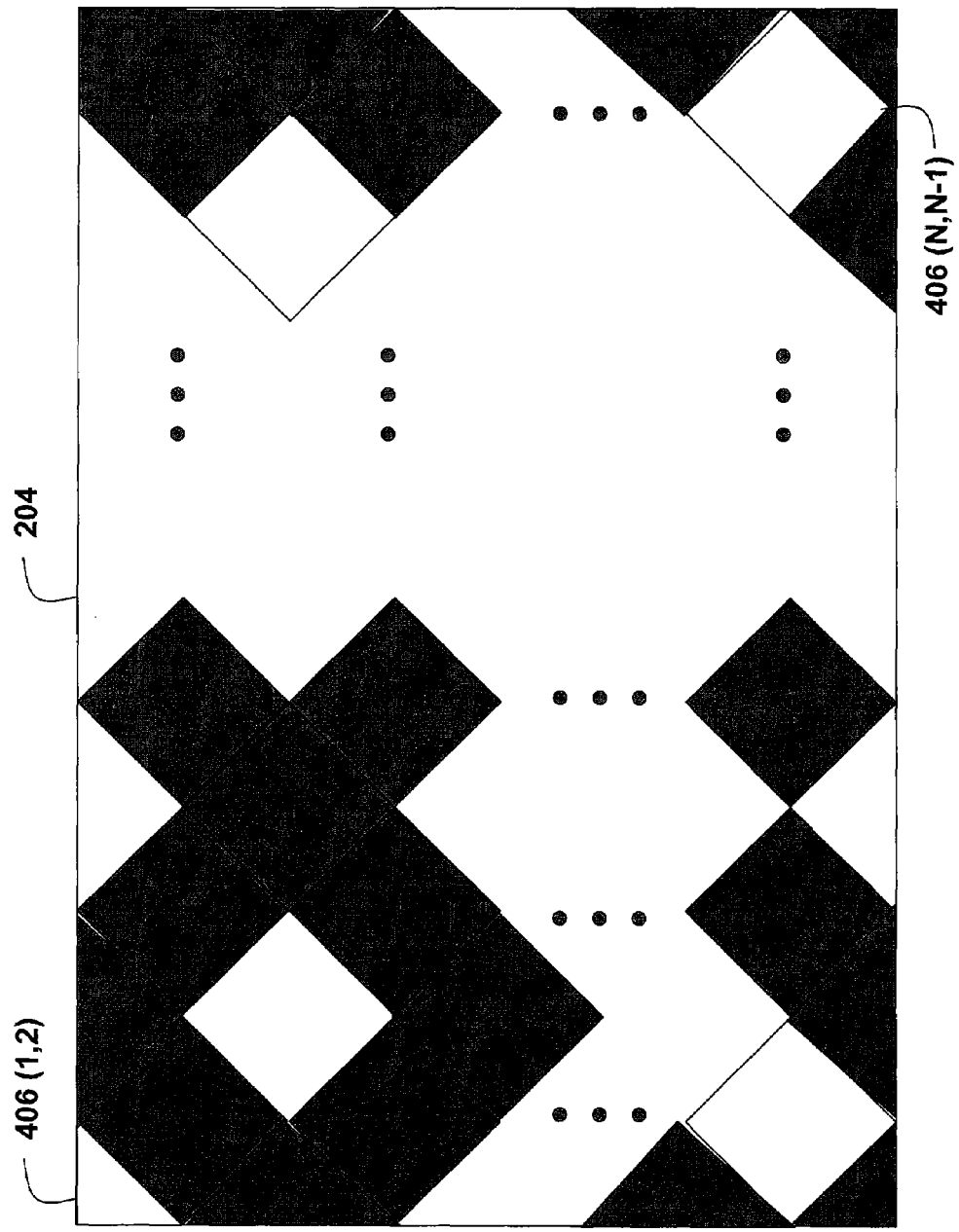
FIG. 4C is a top view of a substrate with diamond nanopillar cores.

Although in FIGS. 4a and 4b, the 2-D grating is produced by rotating the substrate at a 90° angle with respect to the source, it is understood that the substrate may be rotated at any angle and as many times as required. By rotating the substrate at a number of varying angles and pitches, shapes other than square (e.g. diamond or parallelogram shapes) may be produced as shown in FIG. 4c. These techniques may be used to produce shapes having more than four sides, for example, shapes that are approximately circular or elliptical. Similarly, the DUV lithography mask may be specifically constructed to produce nanostructure cores having various shapes and various pitches.

After the nanostructure cores are constructed in step 106, they may be then coated with a SERS active material which may consist of gold, silver, copper, platinum, palladium, titanium, aluminum, lithium, sodium, potassium, indium or rhodium or combinations thereof to produce a SERS active structure. Before applying the SERS active material to the cores, it may be desirable to apply a non-SERS-active material to increase the size of the cores and/or to apply a thin layer of a material which helps the SERS active material to adhere to the cores. At step 107, the process determines whether the size of the cores needs to be increased before applying the SERS material. This may depend, for example on the amount of SERS active material being applied. If, at step 107, it is determined that non-SERS-active material is to be applied, then at step 109, the non-SERS-active material is applied. The non-SERS-active material may be applied using the same techniques, described below with reference to FIG. 5, as are used to apply the SERS active material. This material may be, for example, any of the materials, described above, from which the substrate may be formed.

After either step 106 or 109, step 110 determines whether an adhesion layer should be applied. The adhesion layer is typically a thin layer of a material that helps the SERS active material to adhere to the nanostructure cores. If an adhesion layer is to be applied, step 112 applies the layer and then step 114 applies the SERS active material. If no adhesion layer is needed, then the process proceeds directly to step 114 to apply the SERS active material.

Figure 5:
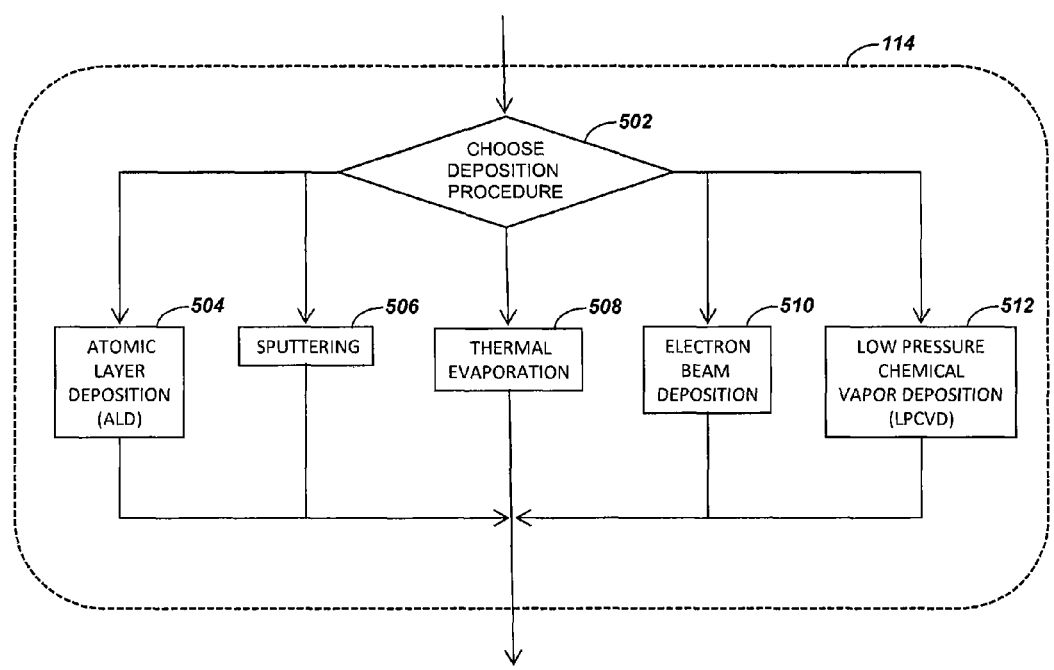
FIG. 5 is a flow-chart diagram of the deposition process in FIG. 1A.

Shown in FIG. 5 is a detailed flow-chart diagram which illustrates possible methods for depositing SERS material in step 114 of FIG. 1A. Specifically, the deposition procedure in is chosen in step 502. Deposition of the SERS active material may be performed in any one of atomic layer deposition in step 504, sputtering in step 506, thermal evaporation in step 508, electron beam deposition in step 510 or low pressure chemical vapor deposition in step 512. Atomic layer deposition may be used, for example, where the nanostructure cores have been augmented with non-SERS-active material and only a thin layer of SERS active material is needed.

During deposition, the uniformity of the deposited SERS may be controlled by rotating and adjusting the angle of the substrate 204 with respect to the deposition source. Specifically, the SERS active material may be preferentially and non-uniformly deposited on different parts of the nanostructure cores (i.e. preferentially deposited on the upper portion of the cores) as well as on various sides of the nanostructure cores at various thicknesses. For example, the SERS active material may be deposited onto one or both sides of the nanowire core to produce a SERS gap between adjacent SERS material. Similarly, the 2-D nanopillar cores may be deposited with SERS active material on either one, two, three or four or more sides. Although the SERS active material is preferentially deposited on, for example one side, it is contemplated that at least some material will be deposited on all sides of the cores by any of these processes. Thus, there will be SERS active material on all sides of the nanostructure cores. By depositing the SERS active material onto the nanostructure cores of a thickness of 50 nanometers to 500 nanometers, the resulting gaps between the SERS active structure can be produced in the range of 1 nanometer-25 nanometers which is conducive to SERS analysis.

Figure 11:
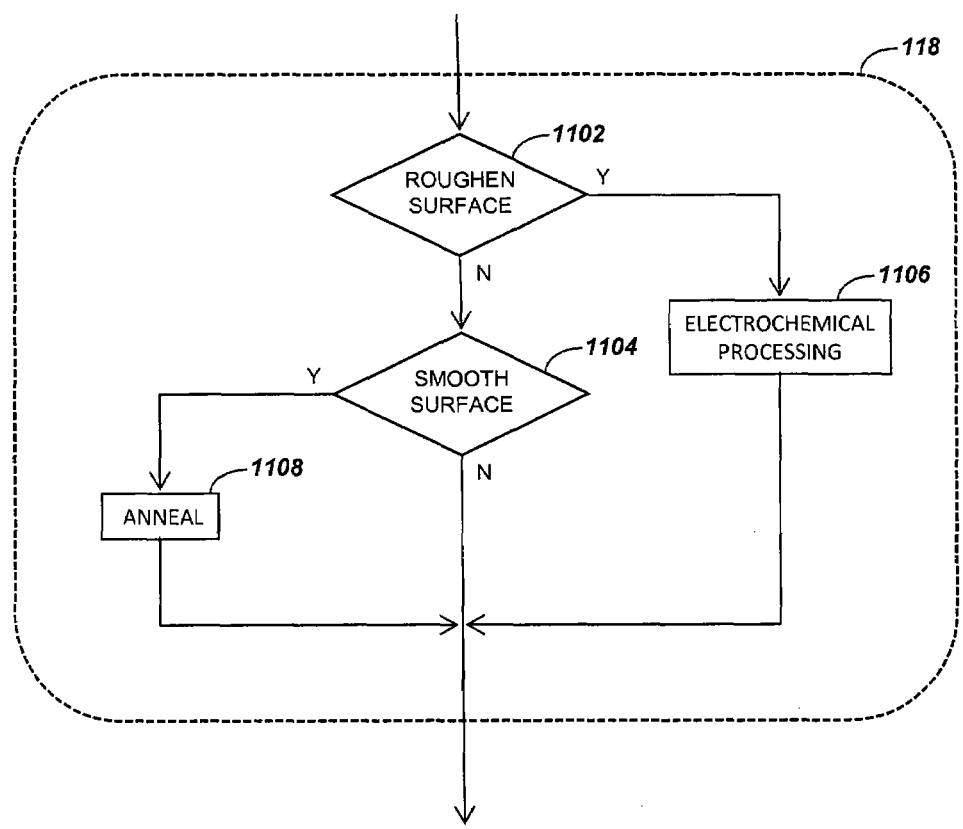
FIG. 11 is a flow-chart diagram of the surface roughening/smoothing procedure in FIG. 1.

After SERS active material is deposited on the nanostructure cores, the surface roughness may be altered to enhance Raman excitation. FIG. 11 shows a flow-chart diagram of the surface roughness altering steps 116 and 118 in FIG. 1A. If step 1102 determines that the surface of the SERS active structure needs to be roughened, step 1106 performs an electrochemical reaction on the SERS surface to increase the roughness. Electrochemical roughening may be carried out, for example, by successively electochemically oxidizing and reducing the metal electrode. This process redeposits the metal irregularly upon reduction so as to promote surface roughness If step 1102 determines that surface roughness is not needed, step 1104 determines whether the surface is too rough and, should be smoothed. If smoothing of the surface is desired, then an annealing procedure wherein the SERS active structure is heated over a specific period of time is performed in step 1108. The temperature to which the structure is heated and the amount of time depend on the particular SERS material and may also depend on the geometry of the device. One skilled in the art would be able to determine an appropriate temperature and time without undue experimentation.

Another step in the manufacturing procedure determines whether a protection layer is to be deposited as illustrated in steps 134 and 136 of FIG. 1A. If a protective layer is needed to protect the SERS active material, it is then deposited on the SERS active material in step 136. The protection layer 604(1)-604(N) as shown in FIG. 7 may protect the SERS active material from contamination and oxidation which may affect its performance during SERS.

Figure 6:
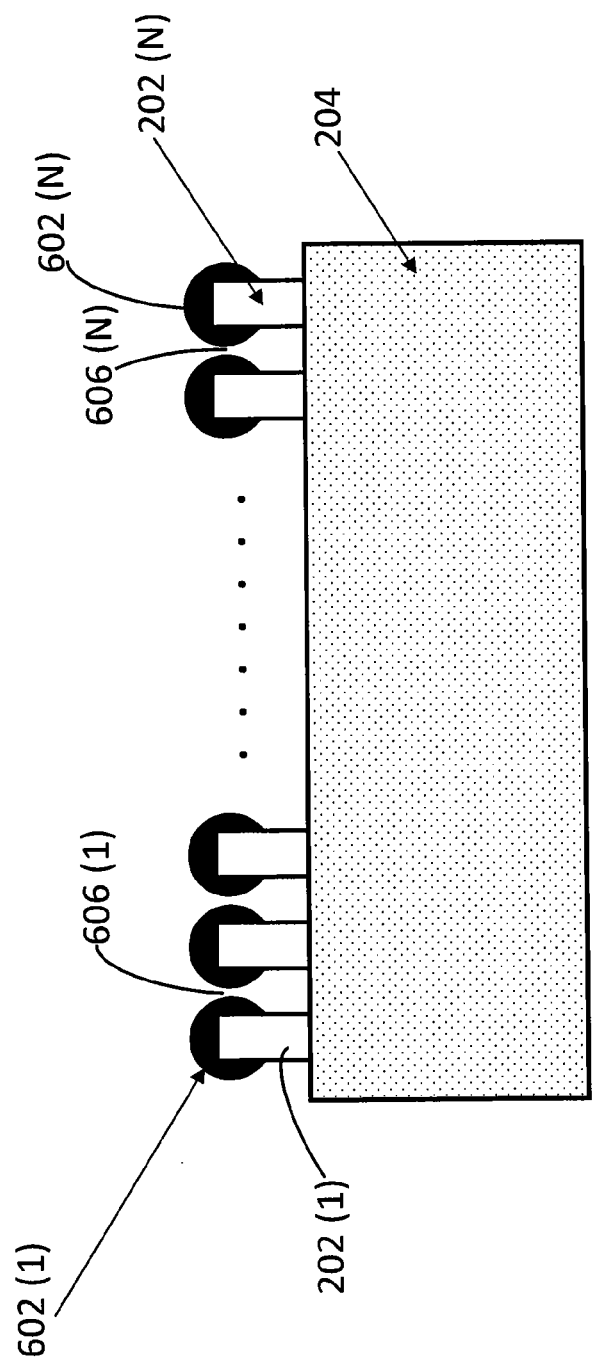
FIG. 6 is a cross sectional view of the substrate in FIG. 2 taken along the line 5-5 with a SERS active material or non-SERS-active material deposited on the nanostructure cores.

After deposition of the SERS active material, a SERS active structure is realized. FIG. 6 shows a cross sectional view of nanostructure cores 202(1)-202(N) coated with SERS active material 602(1)-602(N). In this example, the SERS active material is preferentially deposited on at least two sides and the upper portion of each nanostructure core. This preferential deposition occurs because the deposition of the SERS active material on the nanostructure cores is from one side and at a first angle with respect to the substrate, and then rotated at 180° to perform deposition on the opposite side of each of the nanostructure cores. Each nanostructure core is preferentially deposited with a SERS active material so that the SERS gaps 606(1)-606(N) between adjacent SERS active material is reduced to a distance suitable for performing SERS (1 nm-25 nm).

Silver and some other SERS active materials are prone to contamination, oxidation and other deteriorating effects. Therefore, it may be beneficial to deposit a thin layer of a dielectric material that protects the SERS active material from degrading. The coating may also be used to modify the surface roughness of the SERS active structure. Specifically, the dielectric material may comprise (silicon oxide, aluminum oxide, tantalum oxide, zinc oxide, titanium oxide or some other metal oxide). The material may be deposited at a thickness of (1 nm-10 nm) by, for example, atomic layer deposition.

Figure 7:
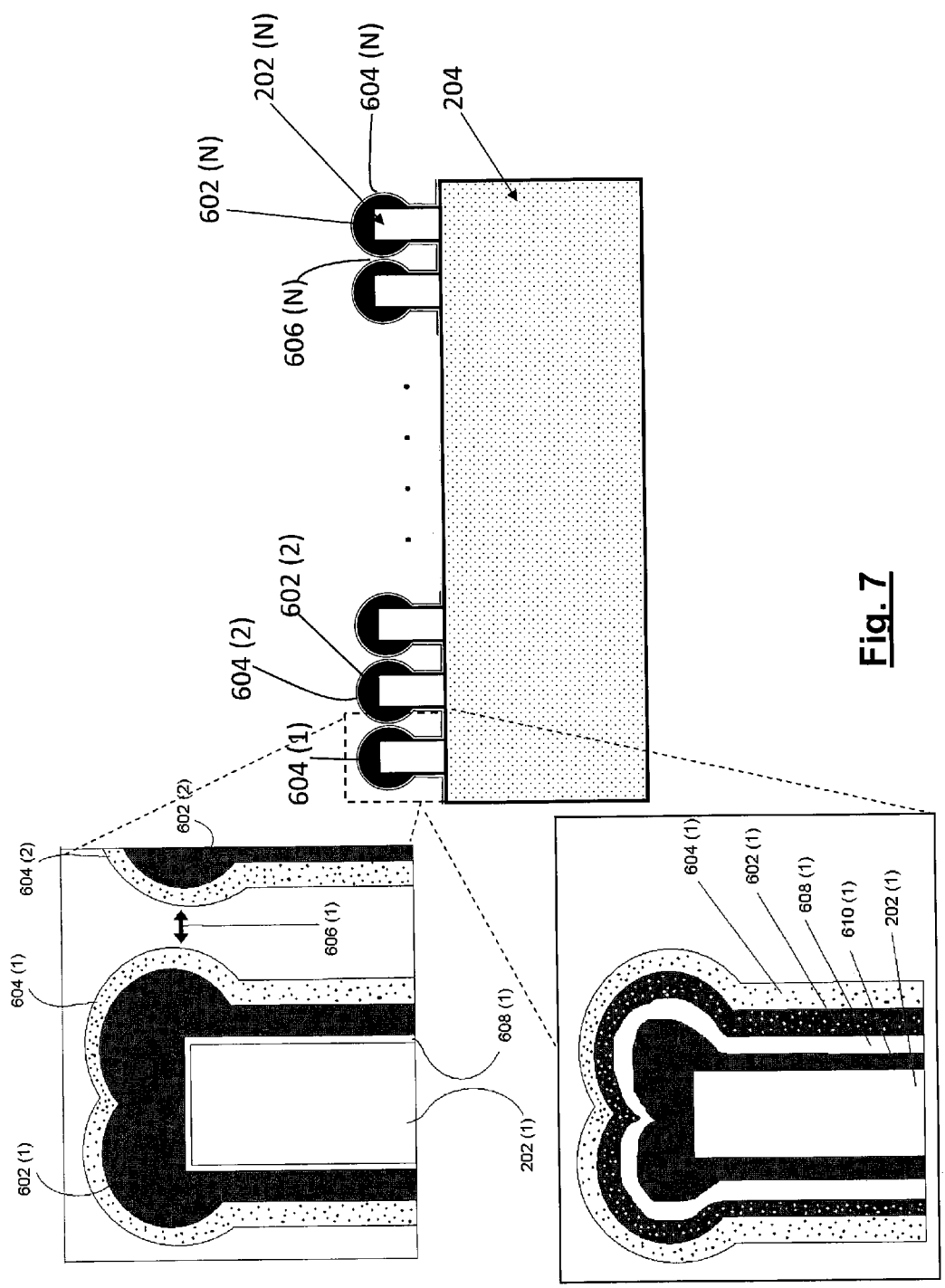
FIG. 7 is the cross sectional view of the substrate as shown in FIG. 6, which shows an optional protective coating and adhesion coating. In one embodiment, the adhesion layer is shown on the nanostructure core and in another example embodiment, the adhesion layer is shown on or the non-SERS-active material.

FIG. 7 shows a first enlarged view of a SERS coated nanostructure having a thick coating of SERS material. It is shown that the deposition of dielectric material 604(1) and 604(2) further reduces the overall gap between the adjacent nanostructures, but does not reduce the gap 606(1) between adjacent SERS material. It is also shown that the adhesion layers 608(1)-608(N) improve the adhesion of the SERS material 602(1)-602(N) to the cores 202(1)-202(N).

FIG. 7 also shows a second enlarged view of a SERS coated nanostructure having a thick coating of non-SERS material. As previously described, the nanostructure cores may be first coated with a non-SERS material. Shown in FIG. 7 is a second enlarged view of a nanostructure core having a thick coating of non-SERS material on the core, an adhesion layer on the non-SERS material, a thin coating of SERS material on the adhesion layer, and a protective layer on the SERS material.

Figure 8:
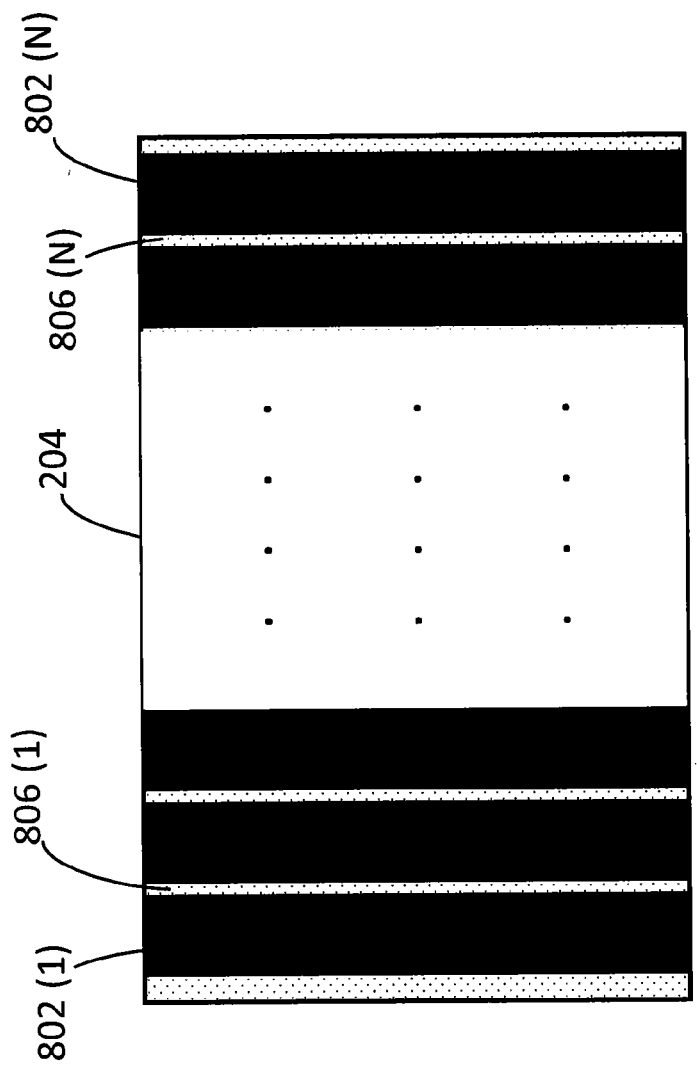
FIG. 8 is a top view of the substrate in FIG. 3 with nanowire cores preferentially covered in SERS active material.

FIG. 8 is a top view of the SERS active structure shown in FIG. 7. In FIG. 8, the SERS active structures are nanowires 802(1)-802(N) that are separated by SERS gaps 806(1)-806(n). Comparing FIG. 3 (nanowire cores without SERS active material) to FIG. 8 (SERS covered nanowire cores), it can be seen that gaps 806(1)-806(N) are reduced. Specifically, the core gaps CG produced by conventional lithography techniques are reduced to produce much smaller SERS gaps 806. In FIG. 8, SERS active material is deposited on both sides of the nanostructure cores. It is also noted that in the 1-D grating, the SERS active material may be preferentially deposited on one side of each nanostructure core to achieve the same core gap 806.

Figure 9:
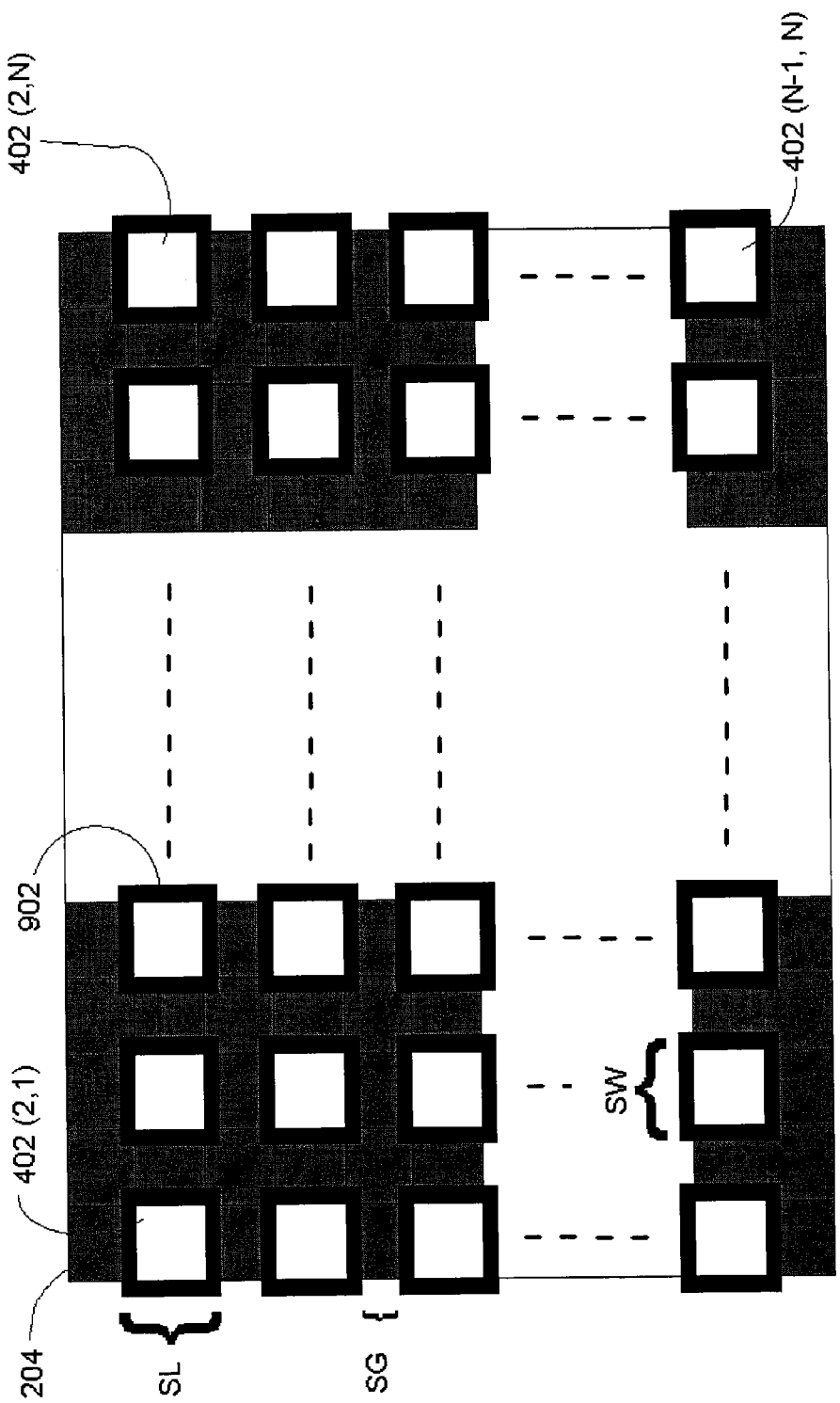
FIG. 9 is a top view of the substrate in FIG. 4A with the square nanostructure cores preferentially covered in SERS active material on all four sides.

Shown in FIG. 9 is a top view of the 2-D nanostructure cores in FIG. 4a coated in SERS active material. The 2-D grating in FIG. 9 comprises nanopillar cores 402(2, 1)-402(N-1, N) which are preferentially coated with the SERS active material on all four sides to produce gaps having a size that is effective in a SERS process.

Figure 10:
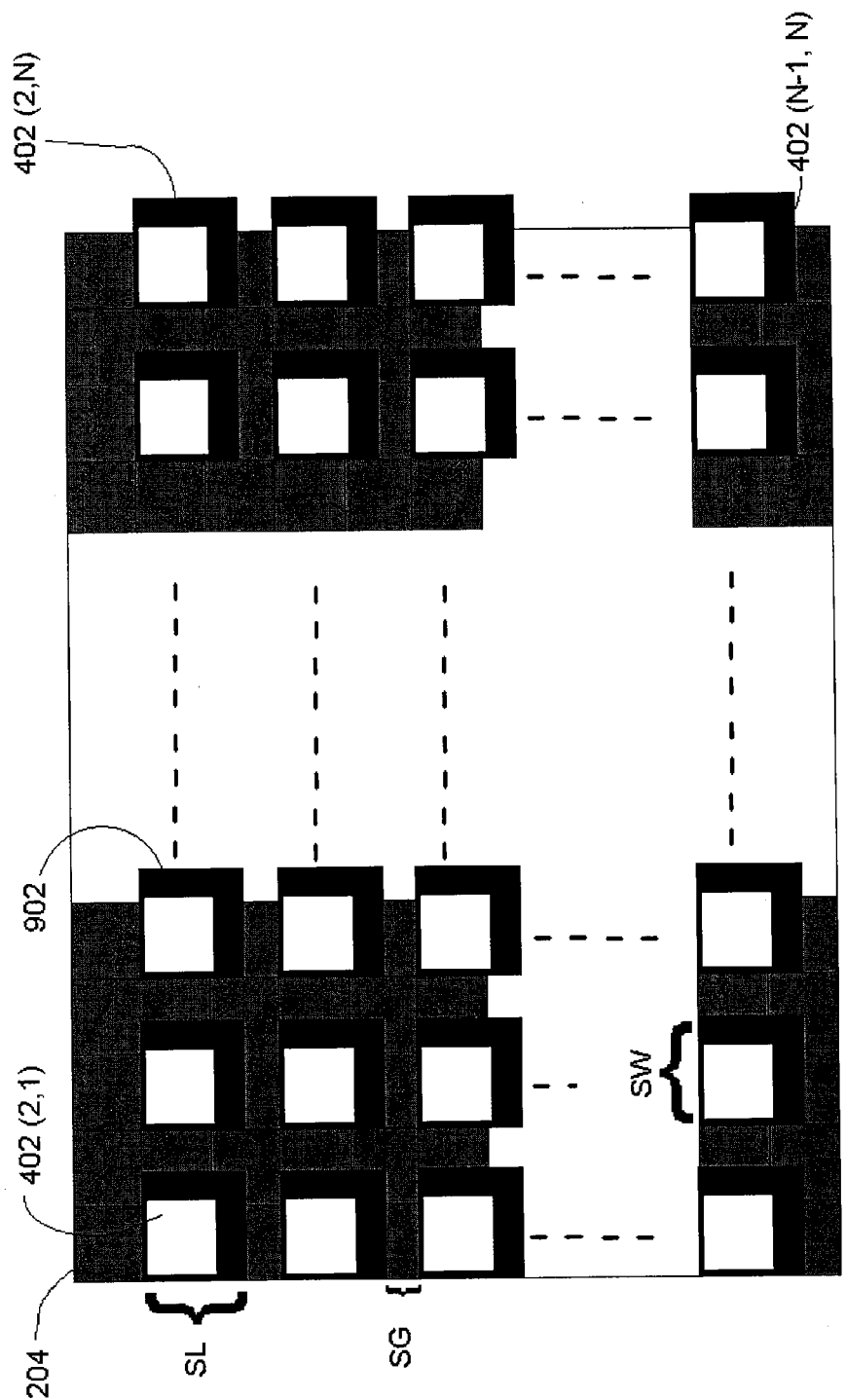
FIG. 10 is a top view of the substrate in FIG. 4A with the square nanostructure cores preferentially covered in SERS active material on two of the four sides.

It should also be noted that the SERS active material does not need to be preferentially deposited on all four sides of the nanopillar cores. As shown in FIG. 10, the SERS gaps between the adjacent nanopillar cores may be reduced by preferentially depositing the SERS active material on only two sides of the nanopillar cores. In either example, at least a thin layer of the SERS active material is deposited on every side and the top of the cores to ensure that the nanostructures are completely coated in SERS.

Figure 12:
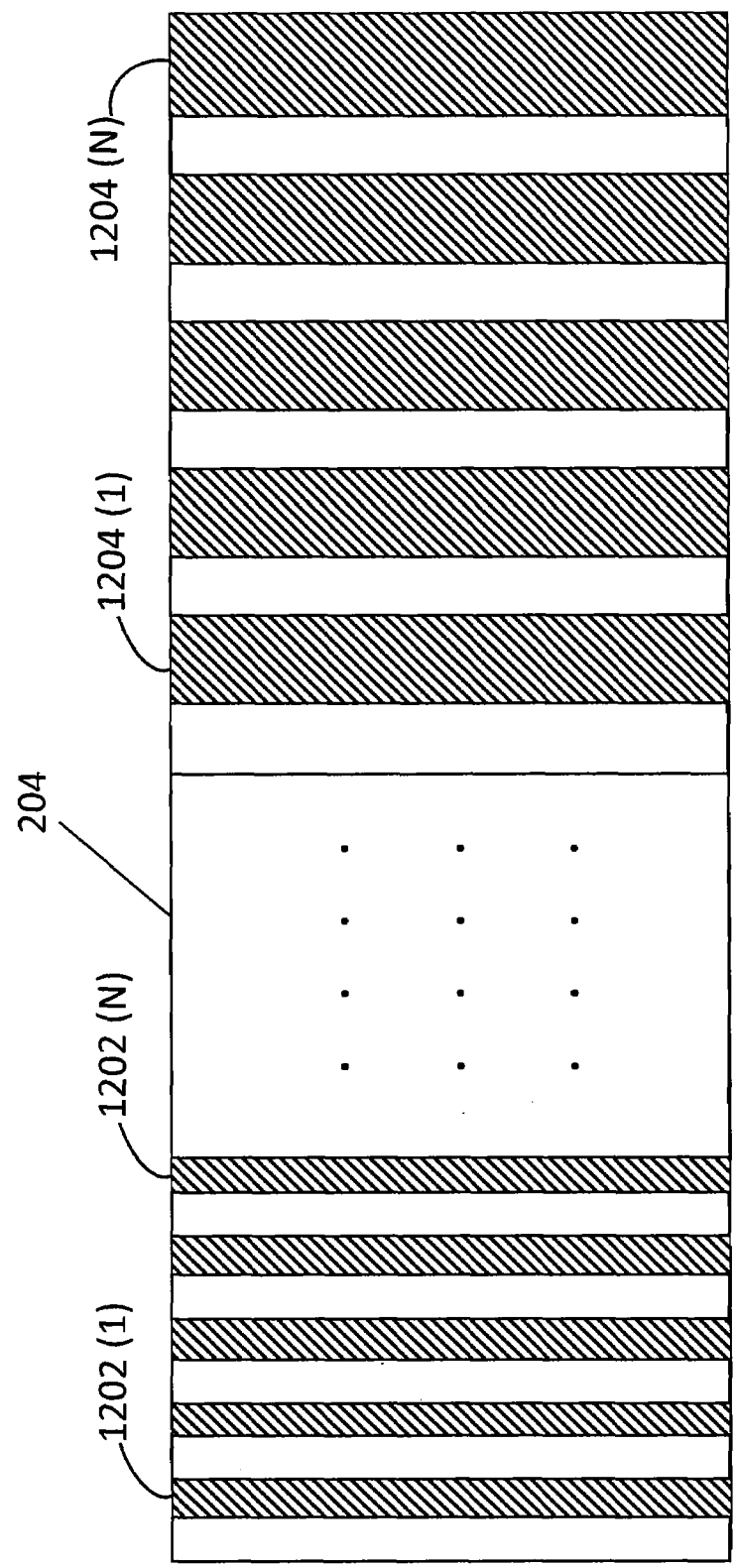
FIG. 12 is a top view of a multi-surfaced substrate with SERS covered nanowire cores having varying SERS spacing between in different areas of the substrate.

Each SERS active structure may be manufactured having a specific gap size and surface roughness. Gap sizes between the adjacent SERS active material effects Raman excitation during SERS analysis. Specifically, certain gaps sizes may be better in detecting certain chemicals in a particular analyte. Thus, it may be beneficial to construct a SERS active structure having multiple areas with differing gap sizes. Specifically, as shown in FIG. 12, the SERS active structure may have an area with nanowires 1202(1)-1202(N) with a first gap size. The same substrate may also have a different area comprising nanowires 1204(1)-1204(N) with a second gap size that is larger than the first. Thus, a particular analyte will produce different Raman excitation when placed on the different areas of the substrate. Furthermore, the SERS active structure may also be designed to use different SERS active materials and/or different service roughnesses, further altering Raman excitation.

Figure 13:
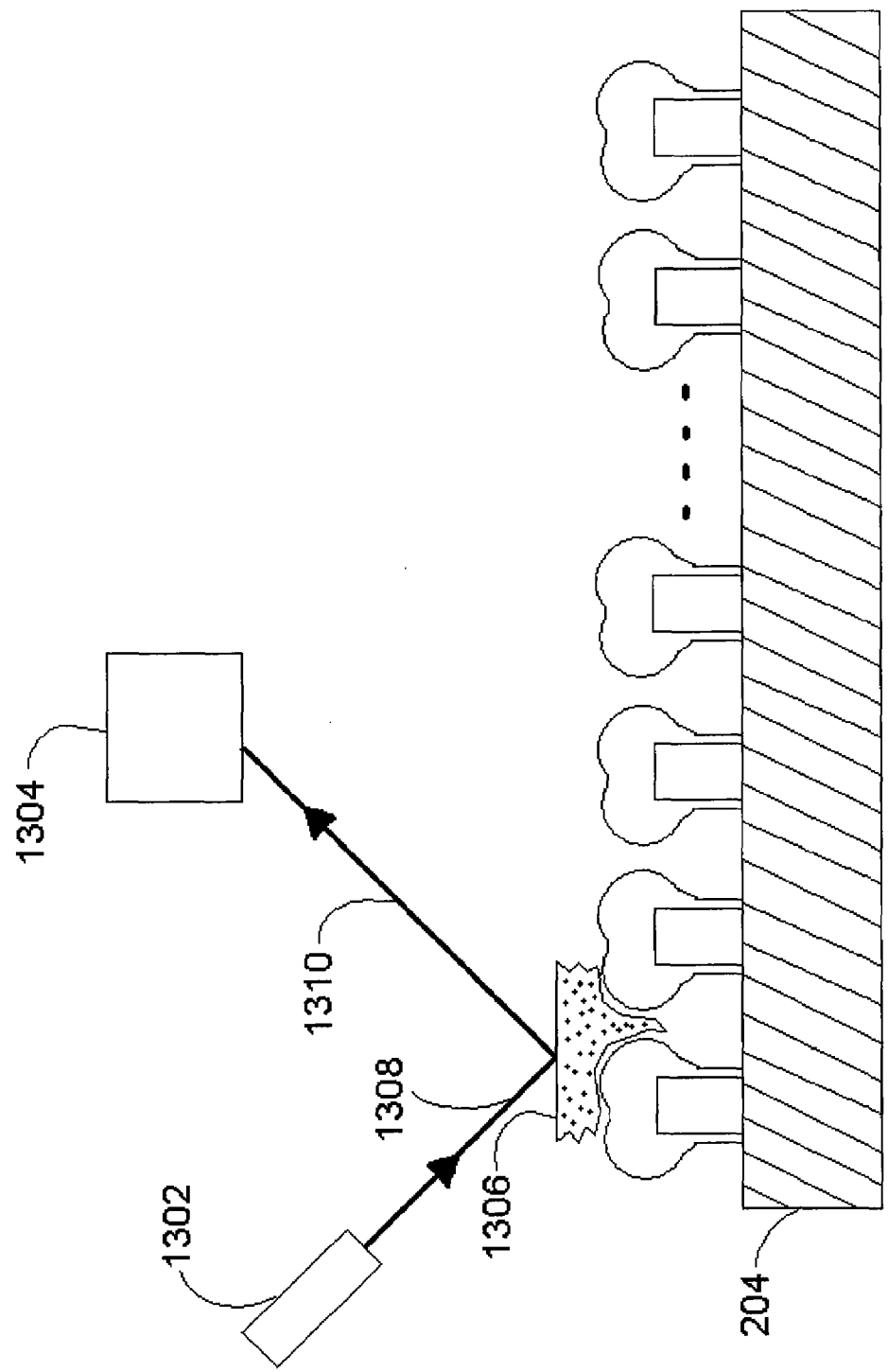
FIG. 13 is a cross sectional view of a system for performing SERS from above an analyte placed on top of a SERS structure.

During SERS analysis, analyte 1306 may be placed on top of the SERS active structure as shown in FIG. 13. Analyte 1306 as well as the SERS active structure are radiated by laser beam 1308 emitted by laser 1302 as the monochromatic light source. Laser beam 1308 may then produce a scattered laser beam 1310 which is detected by detector 1304. Specifically, the scatter laser beam 1310 will be effected by the chemical composition of analyte 1306 as well as the properties of the SERS active structure. The system may also include filters (not shown) to separate the Raman scattered light from Rayleigh scattered light.

Figure 14:
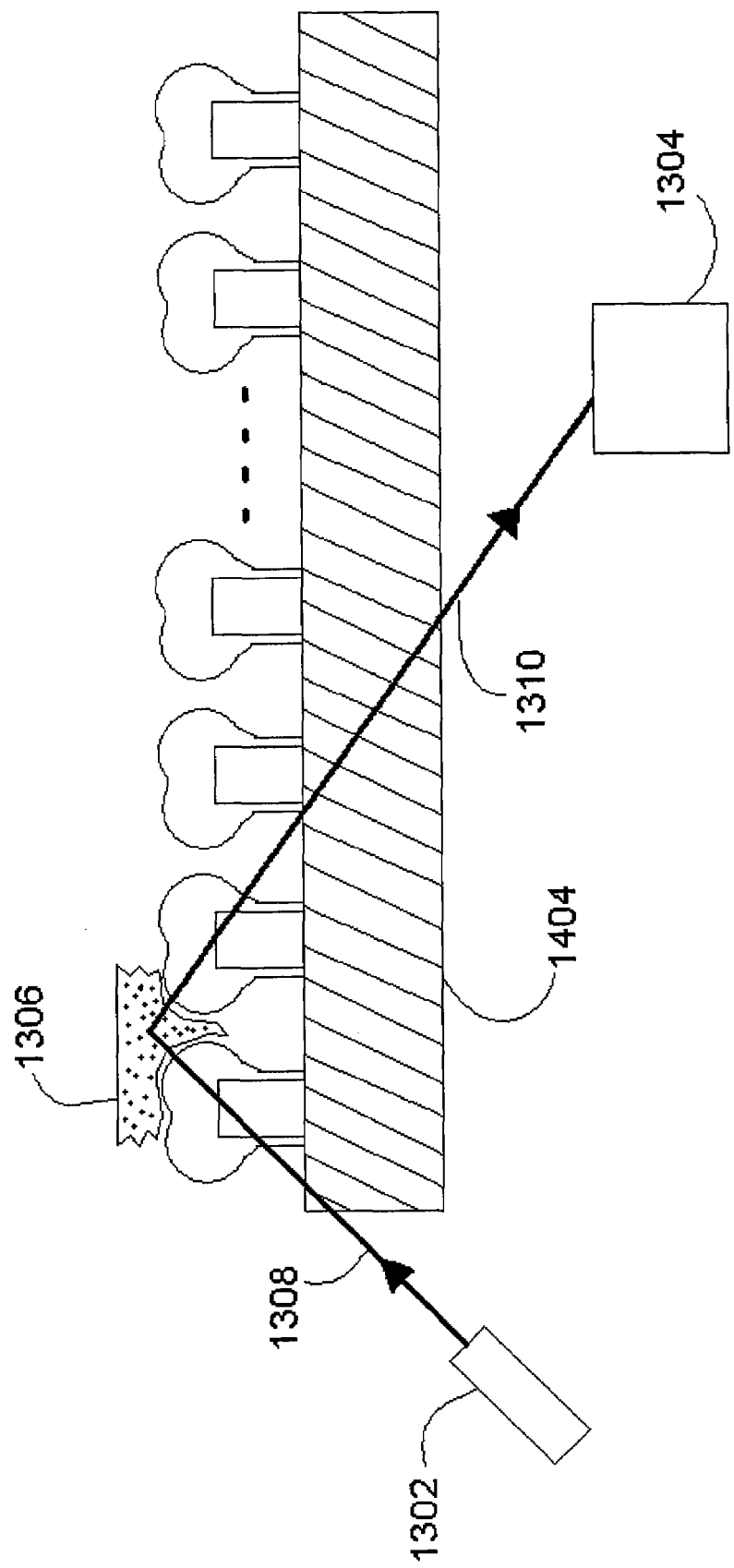
FIG. 14 is a cross sectional view of a system for performing SERS from below an analyte placed on top of a SERS structure having a transparent substrate.

Similarly, in FIG. 14, the substrate may be manufactured as a transparent structure such as glass or at least transparent to light at the wavelength of the monochromatic light source. For example silicon is transparent to some infrared wavelengths. In this embodiment, the laser beam 1308 may be emitted from below the SERS active structure which will then pass through the transparent substrate and the SERS gaps. The laser beam will then scatter off of the SERS active material and analyte 1306. The detector 1304 which is also mounted below the transparent substrate will then detect the scattered laser beam 1310.

In either example shown in FIGS. 13 and 14, the scattered laser beam 1310 may be analyzed to identify specific molecules in analyte 1306. The example SERS substrates, described above, may be sold commercially by packaging under dry nitrogen in diced sizes. Users may then dose liquid samples onto the substrate using a micropipette and perform Raman spectroscopy. One SERS substrate would be usable for several analyses by using non-overlapping areas each substrate dosed with roughly a 0.5 mm spot. By performing Raman spectroscopy on the SERS substrate, the user will be able to effectively target specific biomarkers of various biofluids.

In another example embodiment, the SERS substrate may be functionalized to enhance the ability to detect a particular analyte or group of analytes. For example, The surface of the SERS active material or optional protective layer on the SERS active material may be coated with a chemical or material that causes a particular analyte or group of analytes to preferentially deposit at or near the areas of highest SERS enhancement. The chemical or material may be added by immersion, dipcoating, thin film deposition techniques, exposure to chemical vapors, or other technique known in the art. In addition it is contemplated that different sub-areas of the SERS substrate may be functionalized to enhance the ability to detect respectively different analytes or groups of analytes by applying respectively different surface treatments to the different sub-areas.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for manufacturing a surface enhanced Raman spectroscopy (SERS) active structure, said method comprising the steps of:
    etching a substrate to form a plurality of nanostructure cores extending from the substrate;
    depositing SERS active material onto the plurality of nanostructure cores, and
    controlling a surface roughness of the SERS active material to effect Raman excitation.

2. The method of claim 1, further including: depositing the SERS active material non-uniformly onto the plurality of nanostructure cores.

3. The method of claim 2, further including: depositing the SERS active material preferentially on a top portion of the plurality of nanostructure cores.

4. The method of claim 1, further including: depositing non-SERS-active material preferentially on a top portion of the plurality of nanostructure cores before applying the SERS active material.

5. The method of claim 1, further including: depositing a coating material on top of the SERS active material.

6. The method of claim 5, further including: depositing the coating material by atomic layer deposition.

7. The method of claim 5, further including depositing the coating material to form a protective layer for protecting the SERS active material.

8. The method of claim 7, further including depositing the coating material to protect the SERS active material against contamination.

9. The method of claim 1, further including: reducing the surface roughness by annealing during or after deposition.

10. The method of claim 1, further including: increasing the surface roughness by electrochemical processing.

11. The method of claim 1, further including: depositing non-SERS-active material on the cores, the non-SERS-active material extending the cores in width to reduce the core gaps, and depositing the SERS active material on the non-SERS-active material to further reduce the core gaps.

12. A method for manufacturing a surface enhanced Raman spectroscopy (SERS) active structure, said method comprising the steps of:
    providing a substrate having a photoresist layer;
    performing lithography by exposing the photoresist layer to an energy source, the photoresist exposed to the energy source forming an exposure pattern on the substrate;
    etching the substrate based on the exposure pattern to produce a plurality of nanostructure cores having a plurality of sides extending from the substrate, adjacent nanostructure cores being separated by core gaps;
    depositing SERS active material onto the plurality of nanostructure cores; and
    wherein the step of performing lithography is accomplished by one of laser beam holography, electron beam lithography or deep ultra violet (DUV) photolithography.

13. The method of claim 12, further including: varying a first angle between the substrate and a deposition source to deposit the SERS active material preferentially onto one side of the nanostructure cores, the nanostructure cores being nanowire cores.

14. The method of claim 12, further including: varying at least a first angle and a second angle between the substrate and the deposition source to deposit the SERS active material preferentially onto more than one side of the nanostructure cores, the nanostructure cores being nanopillar cores.

15. A method for manufacturing a surface enhanced Raman spectroscopy (SERS) active structure, said method comprising the steps of:
    providing a substrate having a photoresist layer;
    performing lithography by exposing the photoresist layer to an energy source, the photoresist exposed to the energy source forming an exposure pattern on the substrate;

etching the substrate based on the exposure pattern to produce a plurality of nanostructure cores having a plurality of sides extending from the substrate, adjacent nanostructure cores being separated by core gaps;

depositing SERS active material onto the plurality of nanostructure cores; and performing deposition by one of atomic layer deposition, sputtering, thermal evaporation, electron beam deposition or low pressure chemical vapor deposition.

16. A method for manufacturing a surface enhanced Raman spectroscopy (SERS) active structure, said method comprising the steps of:

providing a substrate having a photoresist layer;

performing laser interference holography by exposing the photoresist layer to an interference pattern generated by a laser at a first pitch and in a first direction to produce an exposure pattern;

etching the substrate based on the exposure pattern to produce a grating;

depositing SERS active material onto the grating; and, wherein the grating is a one-dimensional (1-0) grating and the method further includes depositing the SERS active material preferentially onto at least one side of the 1-0grating.

17. A method for manufacturing a surface enhanced Raman spectroscopy (SERS) active structure, said method comprising the steps of:

providing a substrate having a photoresist layer;

performing laser interference holography by exposing the photoresist layer to an interference pattern generated by a laser at a first pitch and in a first direction to produce an exposure pattern;

etching the substrate based on the exposure pattern to produce a grating;

depositing SERS active material onto the grating; and further including: depositing non-SERS-active material preferentially on a top portion of the grating before applying the SERS active material.

18. A method for manufacturing a surface enhanced Raman spectroscopy (SERS) active structure, said method comprising the steps of:

providing a substrate having a photoresist layer;

performing laser interference holography by exposing the photoresist layer to an interference pattern generated by a laser at a first pitch and in a first direction to produce an exposure pattern;

etching the substrate based on the exposure pattern to produce a grating;

depositing SERS active material onto the grating; and further including: rotating the substrate at an angle and performing laser interference holography at a second pitch in a second direction to produce a 2-D exposure pattern.

19. The method of claim 18, further including: rotating the substrate at a predetermined angle to produce the 2-D exposure pattern, the predetermined angle being approximately 90 degrees, and etching the substrate based on the 2-D exposure pattern to form nanopillar cores having a substantially rectangular cross section.

20. The method of claim 18, further including: rotating the substrate at least one predetermined angle to produce the 2-D exposure pattern, the at least one predetermined angle being less than 90 degrees and etching the substrate based on the 2-D exposure pattern to form nanopillar cores having cross sections other than rectangular.

21. A method for manufacturing a surface enhanced Raman spectroscopy (SERS) active structure, said method comprising the steps of:

etching a substrate to form a plurality of nanostructure cores extending from the substrate;

depositing SERS active material onto the plurality of nanostructure cores to produce the SERS active structure having properties that tend to increase SERS activity for a particular analyte to be placed on the SERS active structure, and customizing the properties of the SERS active structure by manufacturing the SERS gaps between adjacent SERS active material to have a predetermined size.

22. The method of claim 21, further including: customizing the properties of the SERS active structure by manufacturing the surface of the SERS active material to have a predetermined roughness.

23. The method of claim 21, further including: etching the substrate and depositing the SERS active material to form a plurality of areas on the SERS active structure, each of the areas having different properties uniquely enhancing SERS activity for the particular analyte.

24. The method of claim 21, further including: depositing a titanium or chrome layer between the nanostructure cores and SERS active material, the titanium or chrome layer improving the adhesion of the SERS active material.

25. The method of claim 21, further including: applying a material to the SERS active material that causes a particular analyte or group of analytes to preferentially deposit on the SERS active structure.

26. The method of claim 21, further including: depositing a protective coating on the SERS active material; and applying a material to the protective coating that causes a particular analyte or group of analytes to preferentially deposit on the SERS active structure.

27. The method of claim 21, further including:

depositing a protective coating on the SERS active material;

applying a first material to a first sub-area of the coated SERS active material that causes a first particular analyte or group of analytes to preferentially deposit on the first sub area; and applying a second material to a second sub-area of the coated SERS active material that causes a second particular analyte or group of analytes to preferentially deposit on the second sub area.

28. A method for manufacturing a surface enhanced Raman spectroscopy (SERS) active structure, said method comprising the steps of:

forming a layer of material on a substrate;

etching the layer of material to form a plurality of nanostructure cores extending from the substrate; and depositing SERS active material onto the plurality of nanostructure cores to form the SERS active structure; and further including: forming the layer by depositing silicon oxide on the substrate.

29. A method for manufacturing a surface enhanced Raman spectroscopy (SERS) active structure, said method comprising the steps of:

forming a layer of material on a substrate;

etching the layer of material to form a plurality of nanostructure cores extending from the substrate; and depositing SERS active material onto the plurality of nanostructure cores to form the SERS active structure; and further including:

manufacturing the substrate as silicon and growing the layer as silicon oxide.

* * * * *